United States Patent
Hernandez

[11] Patent Number: 5,988,193
[45] Date of Patent: Nov. 23, 1999

[54] ULTRASONIC SINKS FOR MEDICAL, DENTAL AND INDUSTRIAL INSTRUMENTS

[76] Inventor: Teresita V. Hernandez, 4629 St. Martin St., Metairie, La. 70006

[21] Appl. No.: 09/196,578

[22] Filed: Nov. 20, 1998

Related U.S. Application Data

[60] Provisional application No. 60/074,709, Feb. 13, 1998.

[51] Int. Cl.⁶ ..................... B08B 3/12
[52] U.S. Cl. ............. 134/184; 134/186; 134/84
[58] Field of Search ................. 134/184, 186, 134/172, 200, 84, 86, 89; 422/300, 292, 301; 312/228

[56] References Cited

U.S. PATENT DOCUMENTS

| | | |
|---|---|---|
| 1,127,801 | 2/1915 | Oberheim . |
| 1,414,634 | 5/1922 | Fassio ..................................... 134/186 |
| 1,658,413 | 2/1928 | Patelski . |
| 1,668,923 | 5/1928 | Rymann . |
| 1,976,902 | 10/1934 | Stoddard ................................. 134/186 |
| 1,995,331 | 3/1935 | Snyder et al. ........................... 134/186 |
| 2,061,775 | 11/1936 | Panos et al. . |
| 2,121,361 | 6/1938 | Marran . |
| 2,205,113 | 6/1940 | Adams . |
| 2,218,942 | 10/1940 | Webber ................................... 134/186 |
| 2,418,366 | 4/1947 | Powers .................................... 134/186 |
| 3,007,478 | 11/1961 | Leonhardt et al. ...................... 134/186 |
| 3,502,384 | 3/1970 | Gipson . |
| 3,717,159 | 2/1973 | Caviccioli . |
| 4,088,145 | 5/1978 | Noren ...................................... 134/104 |
| 4,736,760 | 4/1988 | Coberly et al. .......................... 134/134 |
| 4,776,359 | 10/1988 | Federighi et al. ....................... 134/111 |
| 5,090,430 | 2/1992 | Nixon ........................................ 134/84 |
| 5,095,925 | 3/1992 | Elledge et al. ............................ 134/61 |
| 5,143,102 | 9/1992 | Blaul ..................................... 134/58 R |
| 5,242,032 | 9/1993 | Prestwood et al. ....................... 184/1.5 |
| 5,248,456 | 9/1993 | Evan et al. ................................. 264/22 |
| 5,286,424 | 2/1994 | Su et al. .................................... 264/23 |
| 5,401,328 | 3/1995 | Schmitz ................................. 134/58 R |
| 5,447,171 | 9/1995 | Shibano ................................ 134/102.2 |
| 5,538,024 | 7/1996 | Inada et al. ................................ 134/60 |

*Primary Examiner*—Frankie L. Stinson
*Assistant Examiner*—Paul J. Lee
*Attorney, Agent, or Firm*—Keaty & Keaty

[57] ABSTRACT

An ultrasonic cleaner for instruments is provided with at least one tank suitable for holding the medical instruments and a cleaning solution therein. A source of ultrasonic waves, such as ultrasonic transducers, is mounted on the exterior of the tank and is connected to a source of electrical power. The cleaning tank has a bottom plate with a drain opening connectable to a municipal sewage line, allowing to drain the cleaning solution along with impurities discharged after the cleaning cycle has been completed. In an alternative embodiment, the cleaning solvents are recycled via a Y-type connector into a second high-pressure hose and then into a storage receptacle with a cover. The alternative embodiment is designed for industrial applications only, where contamination does not pose a risk.

4 Claims, 5 Drawing Sheets

ULTRASONIC SINKS FOR MEDICAL, DENTAL AND INDUSTRIAL INSTRUMENTS

CROSS-REFERENCE TO RELATED APPLICATIONS

This application is a non-provisional application based on my provisional application Ser. No. 60/074,709 filed on Feb. 13, 1998, the full disclosure of which is incorporated by reference herein.

BACKGROUND OF THE INVENTION

This invention relates to ultrasonic cleaners, and more specifically, to a cleaner for medical, dental and industrial instruments.

Ultrasonic cleaners are widely used as some of the most preferred devices for cleaning of surgical instruments and dental instruments. The ultrasonic cleaners are usually capable of releasing tiny particles of debris that get caught in crevices of the instruments or devices. Where other cleaning methods may leave the impurities behind, ultrasonic cleaners work well in cleaning the instruments, objects in a relatively short period of time without hand scrubbing.

With the ever increasing public awareness of the danger of viruses, which are transmitted with bodily fluids, such as Acquired Immune Deficiency Syndrome and Hepatitis, medical professionals invest more time and energy in making sure that all their surgical instruments are safe for the patients and the medical practitioners, as well. The ultrasonic cleaner eliminates hand scrubbing of instruments, which can lead to accidental sticks causing virus transmission to the operator. They also can be applied to other delicate objects, such as clock mechanisms for example.

Ultrasonic cleaners work faster, more effectively, with less risk. Further, ultrasonic cleaners, by generating high frequency vibrations, are believed to be capable of dislodging particularly stubborn accumulations in the surfaces of the instruments, thereby providing a more thorough mechanical cleaning of the objects.

Various patents were issued on the type of cleaning devices that are equipped with electrical circuits for ultrasonic transducers. For example, U.S. Pat. No. 3,640,295 issued to Petersen for "Ultrasonic Cleaner and Surgical Instrument Case" discloses a cradle for receiving an instrument case designed to house surgical instruments. The case is mounted in a sink with an ultrasonic cleaning fluid. The cradle moves back and forth at various angles with respect to the ultrasonic transducers mounted on the sink in order to better clean the instrument case.

Another example of a cleaning device is disclosed in U.S. Pat. No. 5,143,106 issued to Bannon for "Ultrasonic Parts Cleaning Container." According to that patent, a basket-shaped receptacle is placed in a liquid cleaning solution of an ultrasonic bath. Ultrasonic transducers are mounted on the side of the container for delivering the vibration to items placed in the basket. When the device operates, the transducers move freely, dispersing ultrasonic energy throughout the volume of the container.

Other known solutions include provision of an ultrasonic pulse cleaner for generating the ultrasonic energy in a continuous or pulse modes, still others use ultrasonic energy in combination with a heating element, and the like.

While known devices work satisfactory in many instances, they require manual disposal of the cleaning liquid. Since conventional devices are independently standing units, the cleaning solution must be carefully poured into the container and then the container must be emptied, often by hand. Such approach takes valuable time of the operator.

The present invention contemplates elimination of drawbacks associated with the prior art and provision of a cleaning device that utilizes ultrasonic method and allows disposal of the cleaning liquid and the contaminants into municipal sewage line. The present invention further contemplates provision of a device with a quick disconnect pipeline connector to allow collection of the cleaning solution for further use or disposal, depending on the application. It also contemplates filling the sink bowls directly with hot/cold water via faucet and sprayer arm.

SUMMARY OF THE INVENTION

It is, therefore, an object of the present invention to provide a cleaning apparatus for objects that utilizes an ultrasonic energy for removal of foreign particles from the surface of the instruments and other objects.

It is another object of the present invention to provide an ultrasonic cleaner, wherein used cleaning solutions along with the contaminants can be disposed directly into municipal sewerage lines or recycled into receptacle for industrial uses where it may be reused, as well as the ease of filling/rinsing with hot/cold water via faucet/sprayer hose.

These and other objects of the present invention are achieved through a provision of a cleaning apparatus for objects that comprises at least one tank having upright side walls, open top and a bottom plate with a drain opening. The drain opening is adapted for connection to a municipal or other sewage line by a flexible conduit.

A means for creating ultrasonic waves, such as transducers are mounted on an exterior of the tank and, when energized, transmit ultrasonic vibrations to the entire volume of the interior chamber formed by the tank. The transducers are connected to a control panel which, in turn, is connected to a source of electrical power.

A lid is provided for covering an open top of the tank during the period when the transducers are energized to prevent droplets of fluid from escaping the tank. A faucet with a sprayer hose is mounted above the tank to provide a supply of fresh water for rinsing instruments and devices that have been ultrasonically cleaned.

A removable wire mesh basket holds the devices and instruments in the tank, allowing easy positioning and removal of the objects/instruments in the tank. During a cleaning cycle, the drain opening is closed, and a cleaning solution is deposited into the tank that holds the medical instruments. After the cleaning cycle is completed, the drain is opened, allowing the cleaning solution, along with discharged foreign particles and impurities, to be drained into a sewage line.

The rinsing of the objects/instruments is accomplished with fresh hot or cold water delivered through a faucet assembly. The rinsing water can be likewise drained into the sewage line. If desired, the ultrasonic transducers can be energized during a rinsing cycle, as well, to ensure a more thorough rinsing.

For industrial use, when the cleaning solvent is to be retrieved or recycled, the apparatus provides for the use of a valve, which would allow the solvent to drain via a high pressure hose or via a connector, allowing the solvent to drain directly into a receptacle instead of the sewage. The receptacle can be as simple as a plastic bucket with a lid for storage.

The apparatus of the present invention can be constructed with one tank bowl used for both cleaning and rinsing of the instruments or can be constructed in a double-sink design, with the cleaning and rinsing sides formed as a unitary body separated by an upright dividing wall. The cleaning tank is mounted on top of the cabinet that rests on the floor and extends to a height sufficient for the operator to conduct the cleaning operation without excessive bending or stretching. The height of conventional kitchen or storage cabinets is believed to be sufficient.

BRIEF DESCRIPTION OF THE DRAWINGS

Reference will now be made to the drawings, wherein like parts are designated by like numerals, and wherein.

DETAILED DESCRIPTION OF THE PREFERRED EMBODIMENT

Figure 1:
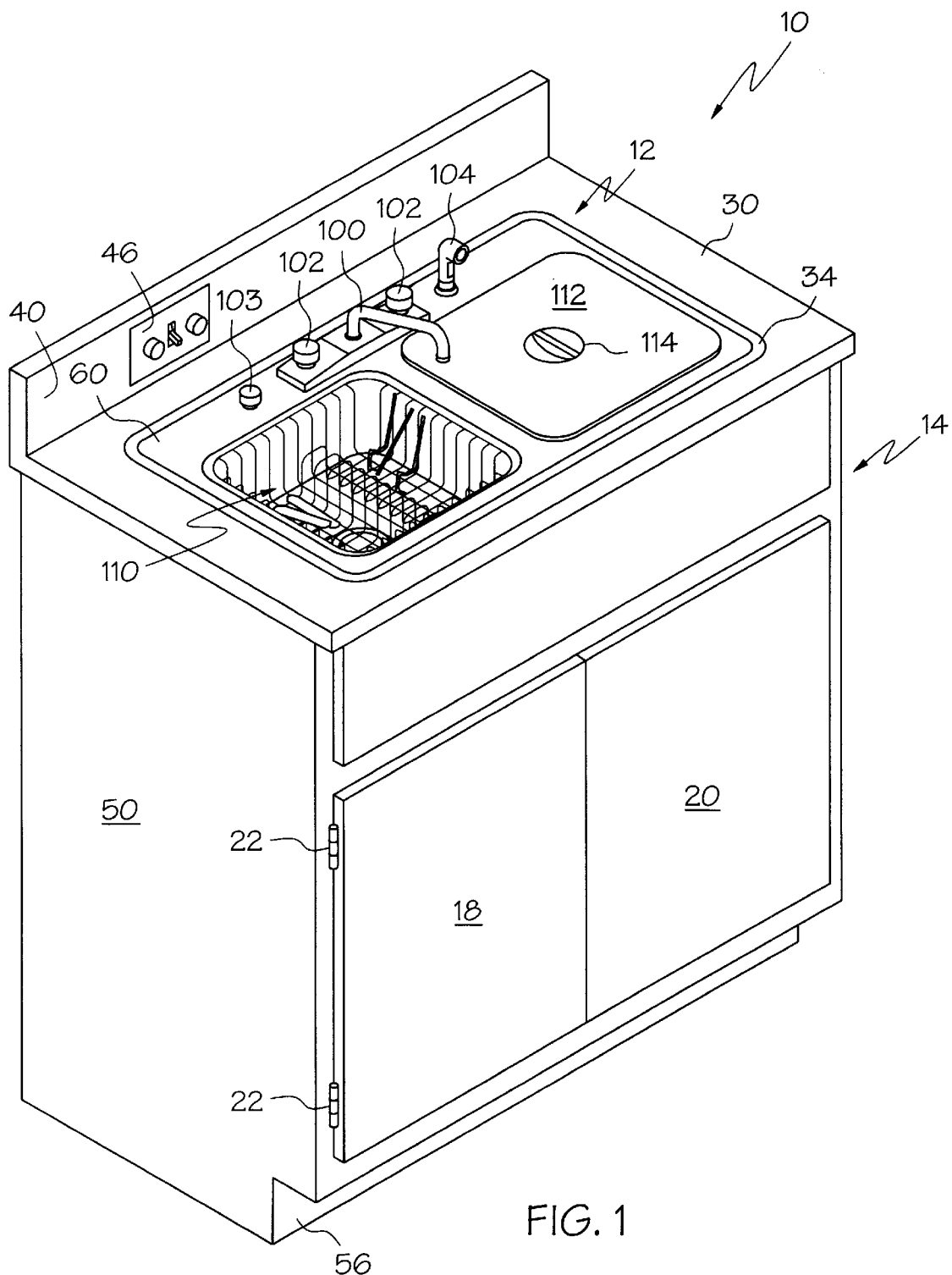
FIG. 1 is a perspective view of a first embodiment of the cleaning apparatus in accordance with the present invention.

Turning now to the drawings in more detail, numeral 10 designates the cleaning apparatus for devices/instruments in accordance with the present invention. The apparatus 10 comprises a cleaning assembly 12 adapted for mounting in a cabinet unit 14, not supplied. The cleaning assembly 12 is mounted in the cabinet 14 in a manner similar to a standard sink. Sink is mounted into traditional countertop.

A flexible, resilient gasket 34 sized and shaped to fit around an upper opening 32 in the cabinet 14 is mounted above the edge of the opening 32 to absorb vibrations imposed by the ultrasonic transducers during a cleaning and/or rinsing cycle, as will be described in more detail hereinafter.

A splash guard 40 is conventionally included in a countertop of the cabinet 14; it is fixedly attached along a line 42 of a countertop 30 of the cabinet 14 to prevent droplets of cleaning liquid and water from settling on areas surrounding the apparatus 10. The splash guard 40 is provided with a cutout 44 which is sized and shaped to accommodate a control panel 46 of the cleaning assembly 12. The cabinet 14 may be provided with side walls 50, 52 and an optional back wall 54.

In one of the embodiments of the present invention, the cleaning assembly 12 comprises a top plate 60 and a pair of cleaning chambers, or bowls 62, 64 separated by a vertical dividing wall 66. The dividing wall 66 forms, along with the vertical side walls, a continuous generally vertically extending wall forming the chambers 62 and 64.

Figure 2:
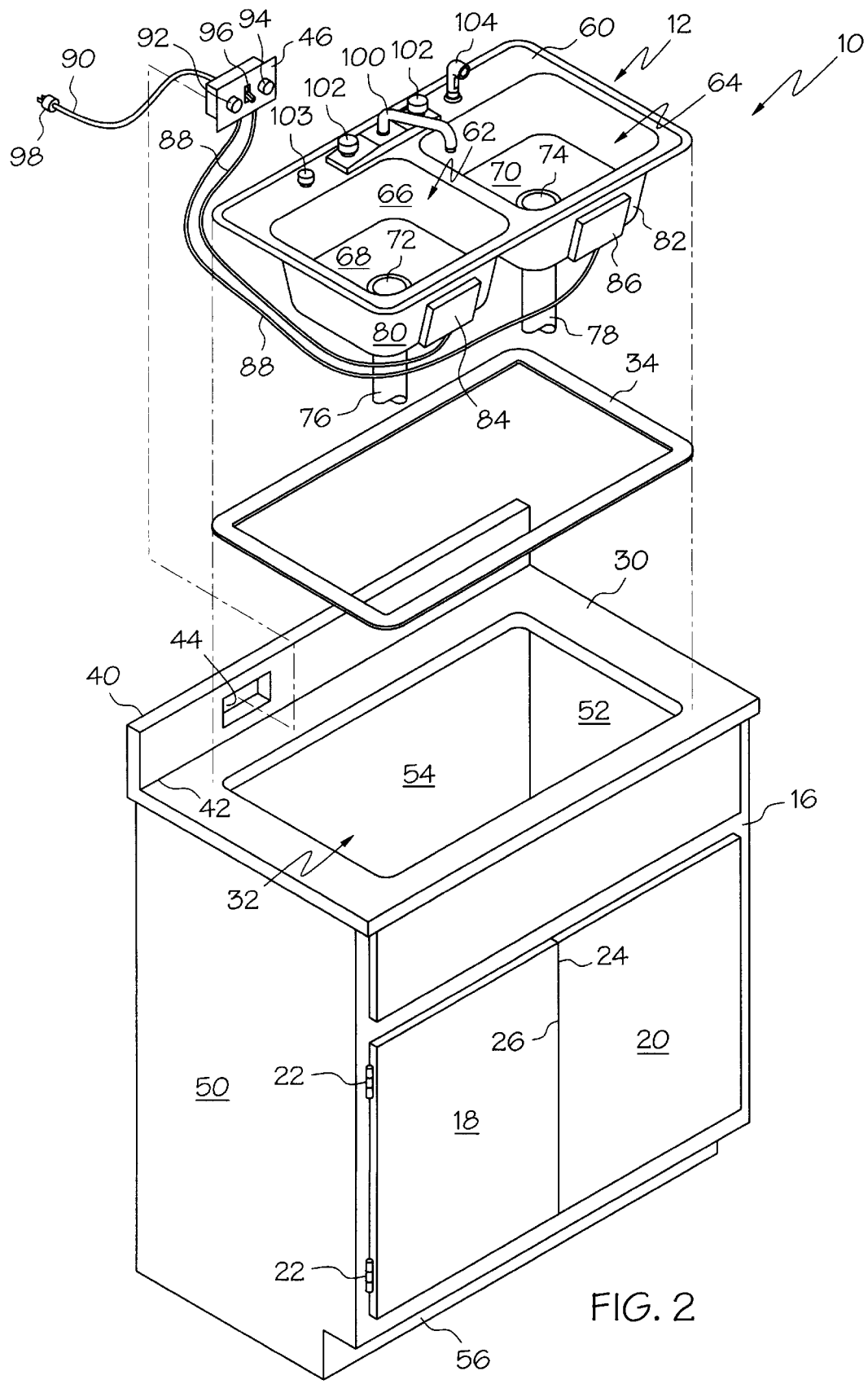
FIG. 2 is a partially blown-apart view of the embodiment shown in FIG. 1.
Figure 5:
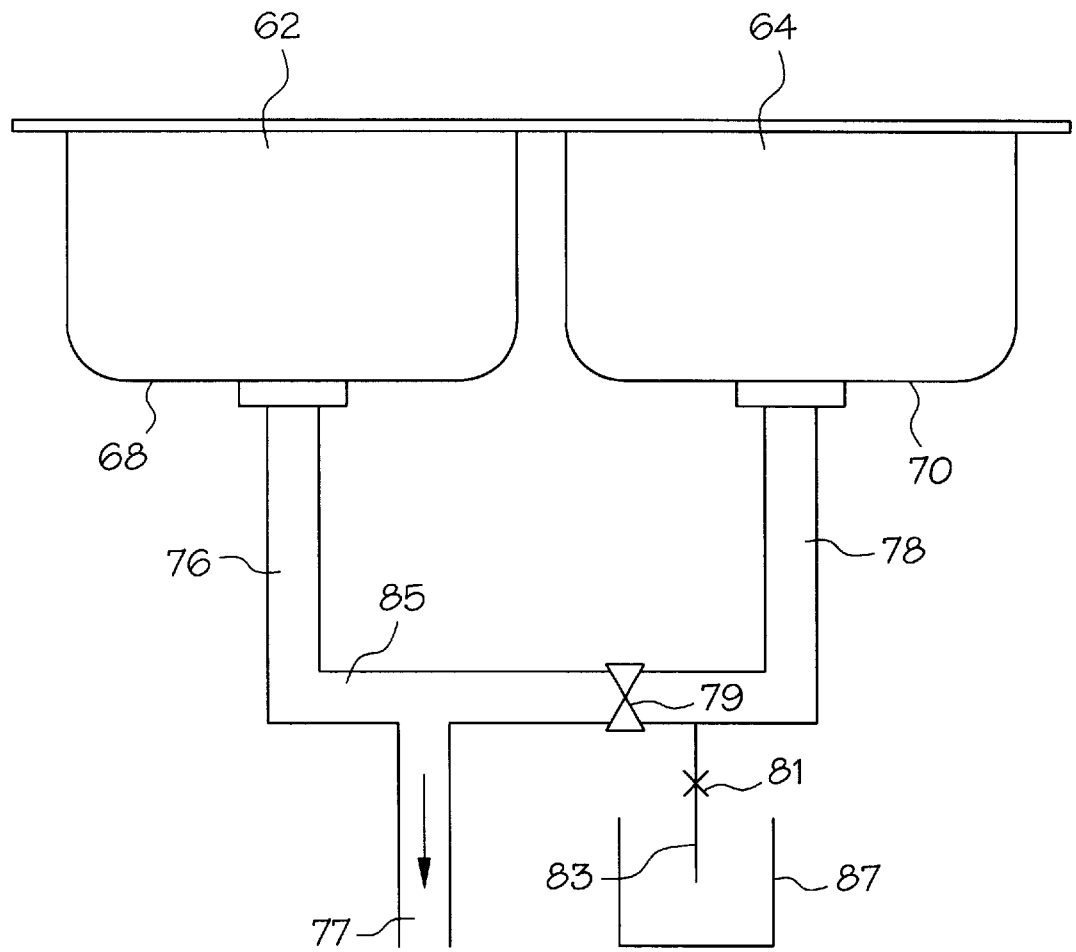
FIG. 5 is a schematic view of pipe conduits connecting the apparatus of the present inventions shown in FIGS. 1 and 2 to sewage line and recycled material receptacle.

Each bowl 62 and 64 is provided with a bottom plate 68 and 70, respectively. The bottom plates 68 and 70 are each provided with a drain opening 72, 74 connected to flexible outlet conduits 76 and 78. The conduits 76 and 78, as shown in FIGS. 2 and 5, extend from the outlet ports 72 and 74 and are adapted for connection to a standard municipal sewerage line 77 through the bottom plates 68 and 70.

A high-pressure valve with quick disconnect Y-connector 79 (FIG. 5) is used for industrial applications, when the cleaning solution needs to be recycled. In that case, an additional valve 81 is mounted in a conduit 83 that is fluidly connected to a common outlet line 85. The pipeline 83, when the valve 81 is open drains into a receptacle 87 for recyclable cleaning solution.

A strainer plate (not shown) with a lever mounted on countertop/sink for draining is provided to catch large particles of debris and other contaminants released from cleaning of devices/instruments. The lever can be remotely activated to prevent use of hands in fluid pop up drain.

Mounted on the underside of the bowls 62 and 64 are ultrasonic transducers 84 and optional transducers 86. The transducers 84 and 86 are shown schematically, and can be two or more in number per bowl 62 and 64, so as to create ultrasonic waves within the interior chambers of the bowls 62 and 64.

The ultrasonic transducers 84 and 86 are connected by suitable connecting cables 88 to the control panel 46. The control panel 46 has a pair of ultrasonic power regulators 92 and 94 for regulation of the transducers 84 and 86, respectively.

A manual on/off switch timer 96 is provided to start operation of the ultrasonic devices. The control panel 46 is connected by an electrical cable 90 to a standard grounded plug 98. The plug 98 is a standard plug adapted for connection with an AC power outlet adjacent the location where the apparatus 10 is mounted.

Mounted on the top plate 60 is a faucet assembly 100 provided with a pair of handles 102 for operating the faucet and admitting hot and cold water into the bowls 62 or 64. The faucet 100, as well as the handles 102 can be made in any conventional configuration, with the faucets connected to a source of water, similarly to household or commercial faucets. An optional hand spray arm 104 can be provided alongside the faucet 100 to allow cleaning and rinsing of the bowls 62 and 64 after use. The faucet assembly 100, if desired, can be formed with a pop-up closing lever 103 to allow closing of the outlet ports 72 or 74.

A wire mesh holding basket 110 is provided for holding the devices/instruments being cleaned and to allow easy removal of the instruments after cleaning. The instruments are schematically shown in FIG. 1 as resting inside the basket 110. A lid 112 with a handle 114 is provided to cover either of the bowls 62 or 64 during a cleaning or rinsing process, particularly when the ultrasonic waves are transmitted throughout the chambers defined by the sink bowls. The lid 112 prevents aerosol contamination of cleaning solution by covering the sink/bowl where the cleaning or rinsing process takes place and preventing the contaminants from splashing the surrounding area.

The bowls or tanks 62 or 64 can be made of any desired depth, from 6 to 10 inches in depth and 14–35 inches wide. In an exemplary embodiment, a manufacturer can use 8–10 inches depth for standard double sink or 6 inches depth for a single (bar-type) sink. The shape of the bowls is dictated by the standard sink size and manufacturing capabilities.

If desired, an optional lower level safety device can be installed in the bowls 62, 64 to prevent ultrasonic transducers from being energized if less than the minimum amount of cleaning solution or water is present in the tank. It is also possible to install a trap filter in the flexible hose lines 76 and 78, so as to catch the debris and prevent it from to being washed into the municipal sewerage line.

The flexible gasket attached to the underside of the top plate 60 prevents liquid from seeping into the counter, as well as damage to the cabinet body 16 when ultrasonic power is transmitted through the wall of the tanks to the interior chamber. The wire basket 110 can be provided with special beaker holding racks, which attach to the sink sides.

In operation, a user closes an outlet 72 with either a pop-up locking device or a drain strainer lid, so as to prevent escape of liquid from the cleaning tank 62. The objects are then placed into the basket 1 10 and the basket is lowered into the tank 62, as shown in FIG. 1. A pre-determined type of a cleaning solution is then poured into the tank 62 to a desired level, for example, three or more inches deep, and the lid 112 is positioned over the bowl 62.

The user then turns "on" mechanical on/off switch 96 and controls the knob 94 to energize the transducer 84. The ultrasonic waves are transmitted through the body of the stainless steel tank 62 into the interior of the chamber defined by the bowl 62, dislodging the debris and other impurities from the surface of the instruments. The cleaning process is performed for a predetermined period of time, for example 15–30 minutes. The solvent is selected to dislodge the particular impurities settled on the medical or dental instruments/devices.

Once the cleaning process is completed, the instruments are lifted, while still in the basket, and transferred to the sink, or tank 64, wherein they are rinsed from the cleaning solution. To ensure better rinsing, the second set of transducers 86 may be energized by operating the control knob 92, again applying the ultrasonic vibrations to the rinsing liquid. The rinsing can be conducted in either water or in a second volume of the cleaning liquid. In industrial applications, the ultrasonic solvent in the rinsing tank 64 can be re-used for cleaning, with the tank 64 serving as the cleaning bowl and the bowl 62 then serving as the rinsing bowl. Alternatively, the cleaning solvent from the bowl 64 can be collected via a Y-connector to a high pressure hose, which can drain the solvent directly into a receptacle, such as a bucket 87.

Once the instruments are cleaned, rinsing with water can be provided in an additional step by admitting water through the faucet 100 into either bowl 62 or 64, washing away any remaining impurities through the outlet port 72 and 74, which have been conveniently opened for this purpose.

Figure 3:
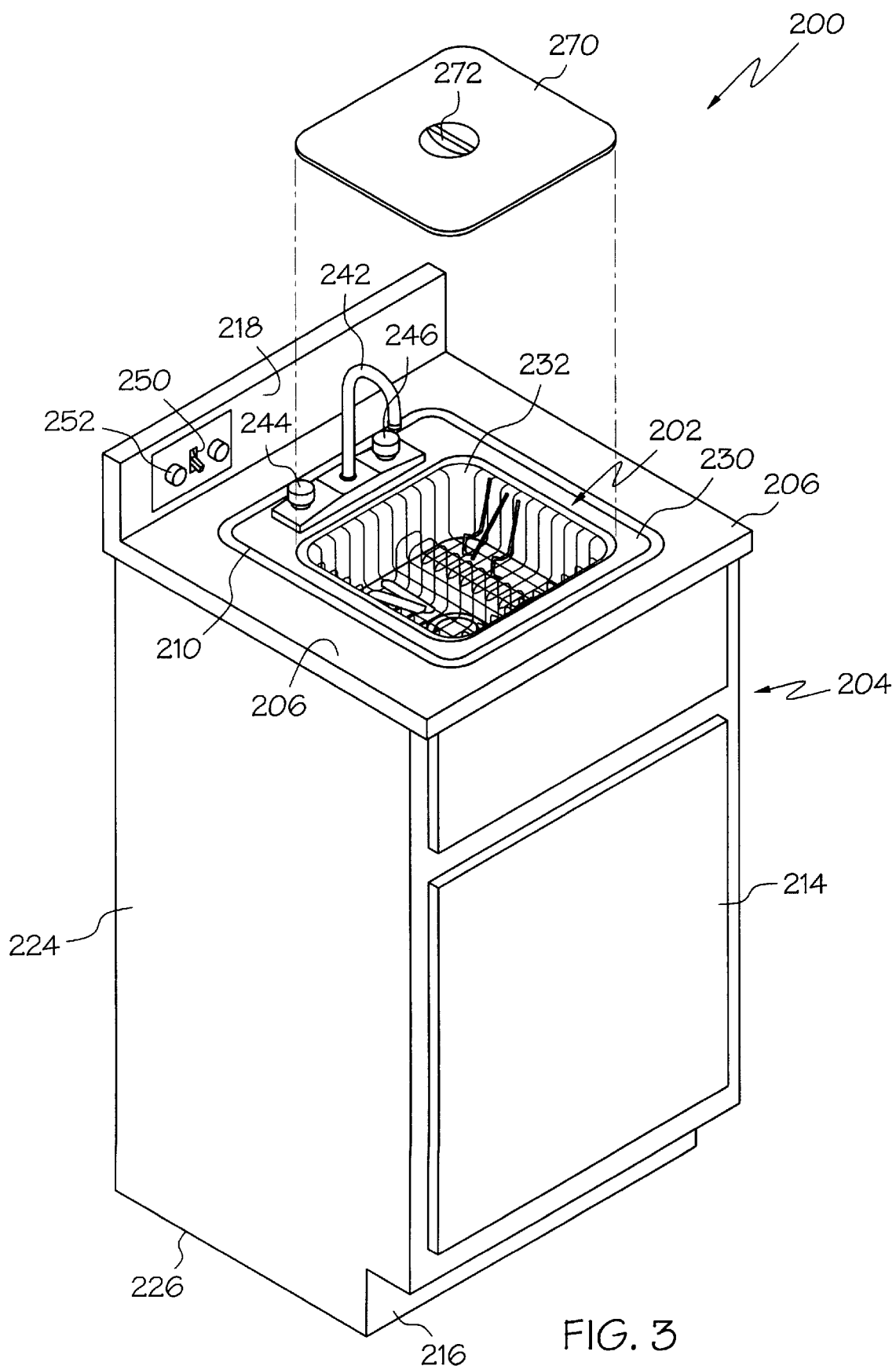
FIG. 3 is a perspective view of a second embodiment of the apparatus in accordance with the present invention.
Figure 4:
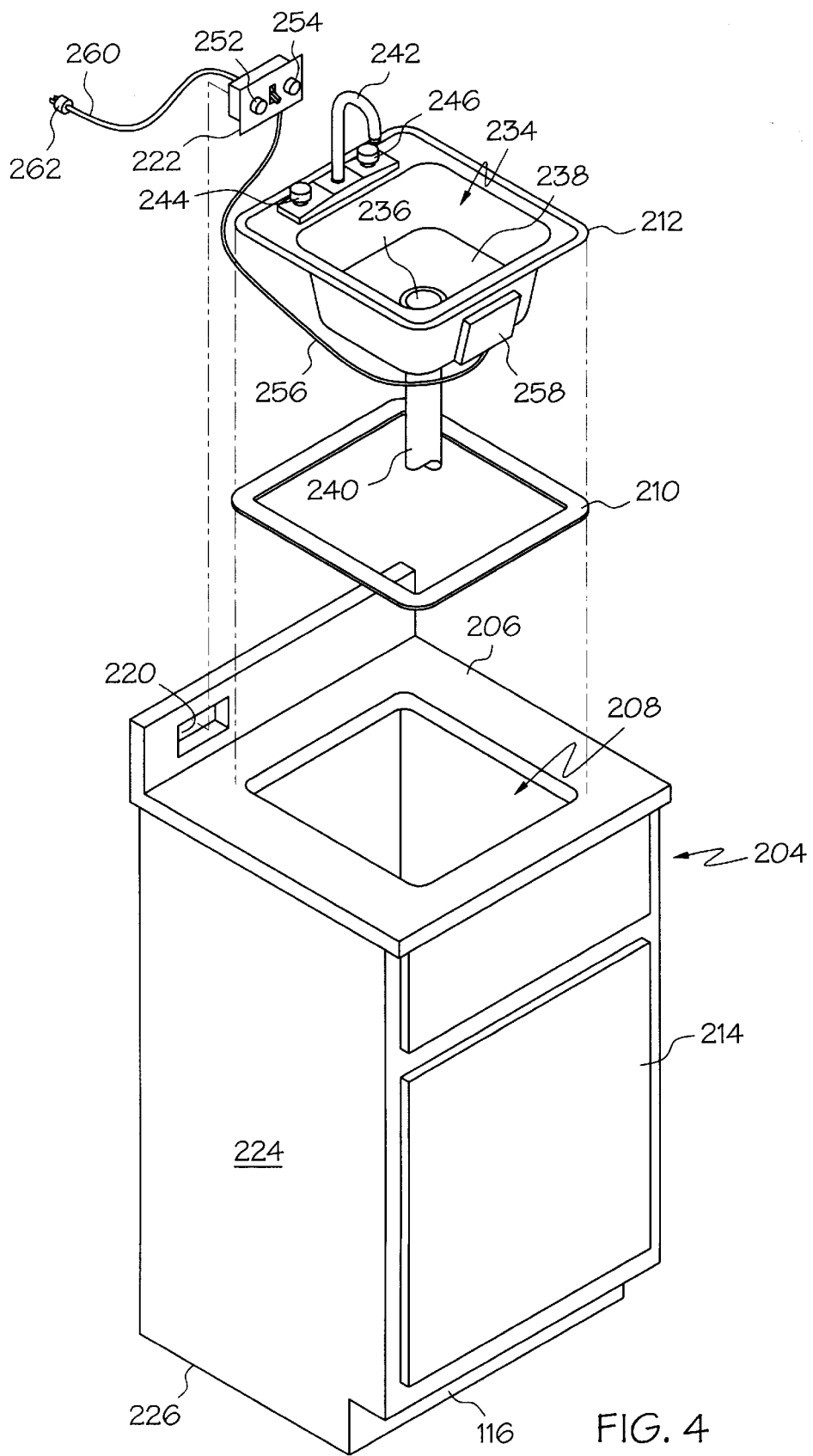
FIG. 4 is a partially blown-apart view of the apparatus shown in FIG. 3.

Turning now to the second embodiment illustrated in FIGS. 3 and 4, a single bar-sized sink, or tank ultrasonic cleaner 200 is shown to comprise a cleaning unit 202 mounted into a countertop with a splash guard, particularly adapted for application on a minimal operating scale.

A resilient flexible gasket, for example, a rubber gasket 210 is interposed between an upper surface of the top plate 106 and the bottom surface of the peripheral lip 212 of the cleaning assembly 202. The gasket 210, similarly to the gasket 34 prevents ultrasonic vibrations from damaging the base cabinet 104.

The cleaning unit 202, similarly to the unit 12, is provided with a cleaning tank 230 that is deep enough to accommodate the required amount of solvent. The depth of the tank 230 can be 6 inches. A wire mesh basket 232 is provided for positioning soiled instruments in the bowl chamber 234 that is formed by the tank 230.

A drain outlet 236 is formed in the center of the bottom plate 238 of the tank 230, and a flexible discharge conduit 240 connects the outlet 236 with a municipal sewerage line. The high pressure hose and conduits accommodating the inlet and outlet of liquids in the tank for the cleaning assembly 202, similarly to the cleaning assembly 12 are made of high-pressure type hose, so as not to be damaged by the ultrasonic vibrations during operation of the cleaning apparatus. A Y-connector conduit (similar to conduit arrangement of the first embodiment) will allow draining of solvent into a second high pressure hose for collection/recycle in industrial applications. The solvent is collected into a bucket receptacle and stored for future use.

A faucet 242 with hot and cold water handles 244 and 246 is provided for the sink 230 to admit fresh water into the bowl and allow rinsing of the instruments with clean water. The rinsing water, similarly to the cleaning solution can be discharged directly through the outlet 236 and the conduit 240.

The control panel 222 is provided with an on/off switch 250 and a pair of regulating knobs 252 and 254. The control panel 222 is connected by an electrical cable 256 to one or more ultrasonic transducers schematically designated by numeral 258 in FIG. 4. The control panel 222 is further connected by a cable 260 to a grounded plug 262 adapted for connecting to a standard AC power outlet.

A protective lid 270 with a handle 272 is sized and shaped for positioning over the open top bowl 230 to prevent escape of droplets of fluid during operation of the ultrasonic device.

In operation, a user closes the outlet port 236 with either a strainer plate or, if a faucet 242 is provided with a pop-up plug, with conventional filling plate, and positions the basket 232 with instruments held therein into the bowl 230. A cleaning solution is then deposited in the chamber 234 in an amount sufficient for cleaning of the particular instruments during a cycle.

The switch 250 of a sixty-minute timer is then turned to the desired time, and the control knobs 252, 254 are operated to start energizing the transducers 258 and transmitting vibrations through the wall of the stainless steel tank 230 to the interior of the chamber 234. The cleaning process continues for 15–30 minutes, depending on the application.

After the cleaning cycle is complete, the solution is drained through the outlet port 236 or recycled via the Y-connector to a second high-pressure hose in the industrial-type applications.

If desired, the instruments can be rinsed with running water admitted from the faucet 242 or the port 236 can be closed again, and the chamber 234 can be filled with clean water sufficient to cover the instruments positioned in the basket 232. The transducers 258 are energized again transmitting ultrasonic vibrations to the water and insure more thorough rinsing. This rinsing can continue for about 10 minutes.

After the rinsing process is completed, and if sterilization is required, the instruments can be placed into a conventional autoclave or a cold sterilization device and sterilized for subsequent use.

The apparatus 10 and the apparatus 200 of the present invention can be also used in an industrial environment. Depending on the object or device to be cleaned, a specific solvent is used in the ultrasonic cleaning device of the present invention. Similarly to a small office use, the object can be cleaned for 15–30 minutes to remove foreign particles and debris from the surface of the object.

The rinsing can be conducted in either the second tank, if the device 10 is used, or in the same bowl, if the device 200 is used. The solvent can be drained directly into sewerage via a high-pressure hose, or, if it still possible to reuse it, retrieved and recycled via Y-type connector into the second high-pressure hose and then into the receptacle for storage of recyclable solvent.

It is preferred that the bowls 62, 64 and 230 be made from a material suitable for conducting ultrasonic vibrations.

Stainless steel makes a suitable choice for this purpose, although other materials can certainly be selected and used.

In comparison with conventional table top or free standing ultrasonic cleaning units, the present invention allows to easily and efficiently dispose of the cleaning solution without endangering operators who might come in contact with contaminated tissue, and saving operator's time. It also allows direct filling and rinsing via faucet and sprayer arm. The apparatus of the present invention can be sold as a cleaning assembly only, which is mounted into conventional countertops.

Conventional countertops often found in medical offices or workshops can be retrofitted for use with the cleaning assemblies of the present invention, thereby providing an alternative to commercially available ultrasonic cleaners, which must be filled and hand-drained separately.

Many changes and modifications can be made in the design of the present invention without departing from the spirit thereof. I, therefore, pray that my rights to the present invention be limited only by the scope of the appended claims.

I claim:

1. A cleaning apparatus for instruments comprising:

a first tank for retaining said instruments during a cleaning cycle, said first tank having a bottom plate with a drain opening;

a second tank for retaining said instruments during a rinsing cycle, said second tank having a bottom plate with a drain opening;

a means mounted on said first tank for creating ultrasonic vibrations in an interior of said first tank;

a faucet assembly mounted between said first tank and said second tank, said faucet assembly being connected to a source of water;

wherein said faucet assembly comprises at least one regulator handle and a spray arm;

a timer operationally connected to said means for creating ultrasonic vibrations;

wherein said means for creating ultrasonic vibrations comprises ultrasonic transducers and a control means connected to said ultrasonic transducers for regulating said ultrasonic transducers, said control means being adapted for a connection to a source of electrical power;

a flexible resilient gasket positioned under said first and and second tank for absorbing vibrations created by said means for creating ultrasonic vibration;

wherein said tanks are mounted into a countertop with a back splash plate;

a removable basket for holding said instruments during a cleaning cycle and a rinsing cycle, said basket being provided with a plurality of openings to allow unobstructed flow of fluid around the instruments; and wherein said drain opening of said first tank and said drain opening of said second tank are each adapted for connection to a sewage line by a high-pressure hose.

2. The apparatus of claim 1, wherein a secondary means for creating ultrasonic vibrations are mounted on said second tank for creating ultrasonic vibrations during a rinsing cycle.

3. The apparatus of claim 1, further comprising a drain assembly for regulating drainage of liquids from said first tank and said second tank.

4. The apparatus of claim 1, wherein said second tank carries a secondary, independently controllable means for creating ultrasonic vibrations in said second tank.

\* \* \* \* \*